United States Patent [19]

de Toledo et al.

[11] Patent Number: 4,830,023

[45] Date of Patent: May 16, 1989

[54] MEDICAL GUIDEWIRE

[75] Inventors: Fernando A. de Toledo, Concord; Hugh A. Tripp, Foxboro, both of Mass.

[73] Assignee: Medi-Tech, Incorporated, Watertown, Mass.

[21] Appl. No.: 126,042

[22] Filed: Nov. 27, 1987

[51] Int. Cl.$^4$ .................................... A61M 25/00
[52] U.S. Cl. .................................... 128/772; 128/657
[58] Field of Search .................. 128/772, 656–658, 128/341–344; 604/164–170, 280, 282, 95

[56] References Cited

U.S. PATENT DOCUMENTS

| | | | |
|---|---|---|---|
| 2,118,631 | 5/1938 | Wappler | 604/170 |
| 2,560,915 | 7/1951 | Bamberger | 604/45 |
| 3,528,406 | 9/1970 | Jeckel et al. | 128/772 |
| 3,749,086 | 7/1973 | Kline et al. | 128/772 |
| 3,789,841 | 2/1974 | Antoshkiw | 128/772 |
| 3,906,938 | 9/1975 | Fleischhacker | 128/772 |
| 4,003,369 | 1/1977 | Heilman et al. | 128/772 |
| 4,020,829 | 5/1977 | Willson et al. | 128/772 X |
| 4,080,706 | 3/1978 | Heilman et al. | 128/772 X |
| 4,534,363 | 8/1985 | Gold | 128/772 |
| 4,538,622 | 9/1985 | Samson et al. | 128/772 |
| 4,545,390 | 10/1985 | Leary | 128/772 |
| 4,619,274 | 10/1986 | Morrison | 128/772 |
| 4,676,249 | 6/1987 | Arenas et al. | 128/657 |
| 4,719,924 | 1/1988 | Crittenden et al. | 128/657 X |
| 4,724,846 | 2/1988 | Evans, III | 128/657 X |

Primary Examiner—Kyle L. Howell
Assistant Examiner—Angela D. Sykes

[57] ABSTRACT

A medical guidewire has an elongated body that has a degree of flexibility and a distal tip region of relatively greater flexibility. The guidewire consists of a core having a body of first diameter, a distal portion of a relatively smaller diameter, and a generally flat distal end. The end is disposed in the tip region and is spaced proximally from a round tip element that defines the distal end of the guidewire. A first coil is joined to the core body and extends along the core to a termination point in the distal tip region, proximal of the end of the core. A relatively more flexible second coil is joined at its proximal end to the first coil and joined at its distal end to the round tip element. A safety wire is secured to the core and has a generally flat distal end within the second coil, joined to the round tip. A transition wire is secured to the core and has a generally flat distal end that terminates within the second coil intermediate of the distal ends of the core and safety wire. In this or other medical guidewires, the first and second coils are joined in sequence, the second coil overlapping the first coil, both having essentially the same outer diameter. The above resulting in a joint of substantially uninterrupted flexibility.

22 Claims, 2 Drawing Sheets

MEDICAL GUIDEWIRE

The invention relates to medical guidewires, e.g., for navigation of narrow passages of a body. A physician introduces the distal end of the guidewire into the body, e.g., via a puncture opening, and, observing the progress of the guidewire via radioscope, attempts to manipulate the flexible tip of the guidewire, e.g., by rotation of the proximal end of the guidewire outside the body, to enter desired passageways and follow their convolutions to a treatment site. A catheter or other medical device may then be advanced over the guidewire to the site.

SUMMARY OF THE INVENTION

According to the invention, a medical guidewire has an elongated body that has a degree of flexibility and a distal tip region of relatively greater flexibility, the guidewire comprising a core having a body portion of a first diameter, a distal portion of a relatively smaller diameter, and a generally flat distal end portion, the end portion disposed in the tip region and spaced proximally from a round tip element that defines the distal end of the guidewire, a first coil joined to the body portion of the core an extending along the core to a termination point in the distal tip region, proximal of the end of the core, a relatively more flexible second coil joined at its proximal end to the first coil and joined at its distal end to the round tip element, a safety wire secured to the core, the safety wire having a generally flat distal end portion within the second coil, joined to the round tip element, and a transition wire secured to the core, the transition wire having a generally flat distal end portion disposed to terminate within the second coil intermediate of the distal end portions of the core and of the safety wire.

Preferred embodiments of this aspect of the invention have one or more of the following features. The generally flat distal end portions of the core, safety wire add transition wire are of predetermined axial extent, and the generally flat distal end portion of the transition wire is disposed to span a gap between the proximal end of the safety wire end portion and the distal end of the core end portion. At least one of the safety wire and the transition wire is a flat ribbon wire. At least one of the safety wire, the transition wire, the second coil and the round tip element are of radioopaque material, e.g., comprising platinum. The first coil in a first region preceding the second coil has a first outer diameter and in a second region distal to the first region the first coil has a second, relatively smaller outer diameter, and the second coil, in a proximal region adjacent the first coil, has an outer diameter substantially equal to the first outer diameter of the first coil and an inner diameter substantially equal to the second outer diameter of the first coil, and the proximal region of the second coil is disposed about the second, smaller diameter region of the first coil. Preferably the diameter of the first coil in the first region is substantially uniform, and the diameter of the first coil in the second region is substantially uniform, and the first region lies immediately adjacent the second region. Also, the relatively smaller second diameter of the second region of the first coil is formed by removal of coil wire material from the exterior of the coil, preferably by grinding. The first coil and the second coil are joined in the proximal region of the second coil. Adjacent windings of the first coil in the region proximal of joining to the second coil are relatively more spaced than adjacent windings of other, more proximal regions of the first coil. The first coil terminates distal of the proximal end of the core and the guidewire further comprises a sleeve of polymeric material, preferably polytetrafluorethylene (PTFE), disposed about the core. The sleeve terminates distally adjacent the proximal end of the first coil and the outer diameter of the first coil adjacent the sleeve is equal to or greater than the outer diameter of the adjacent sleeve.

According to another aspect of the invention, a medical guidewire comprises, in sequence, a first coil and a relatively more flexible second coil, the first coil in a first region preceding the second coil having a first outer diameter and in a second region distal the first region the first coil having a second, relatively smaller outer diameter, and the second coil, in a proximal region adjacent the first coil, having an outer diameter substantially equal to the first outer diameter of the first coil and an inner diameter substantially equal to the second outer diameter of the first coil, and the proximal region of the second coil is disposed about the second, smaller diameter region of the first coil.

In preferred embodiments of this aspect of the invention, the diameter of the first coil in the first region is substantially uniform, and the diameter of the first coil in the second region is substantially uniform, and the first region lies immediately adjacent the second region; and the relatively smaller second diameter of the second region of the first coil is formed by removal of coil wire material from the exterior of the coil, e.g., by grinding.

Further preferred embodiments of this aspect of the invention may include one or more of the following features. The first coil is formed of round wire, and the second coil may be as well. The difference between the first outer diameter and the second outer diameter is less than or equal to one half the diameter of the round wire. The first and second coil are joined in the proximal region of the second coil. Adjacent windings of the first coil in the region proximal of joining to the second coil are relatively more spaced than adjacent windings of other more proximal regions of the first coil. The first coil and/or the second coil have outer portions of tapering diameter.

Attributes sought by physicians employing guidewires include high torque response of the distal tip within the body to rotation of the portion outside the body; stiffness over much of the length for transmission of axial pressure; a flexible tip to facilitate manipulation into side branches and through convuluted passages and also to avoid patient trauma; and also a radioopaque tip region for clear viewing. The guidewire of the invention features these attributes and further provides a relatively smooth transition from the relative stiff proximal portion of the guidewire to the flexible distal tip.

These and other features and advantages of the invention will be apparent from the following description of a presently preferred embodiment, and from the claims.

PREFERRED EMBODIMENT

We first briefly describe the drawings.

Figure 1:
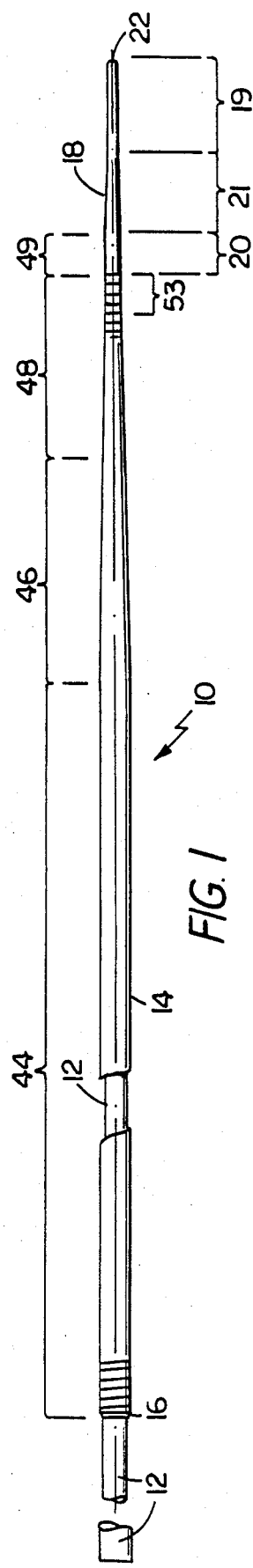
FIG. 1 is a side view partially in section of a medical guidewire of the invention.
Figure 2:
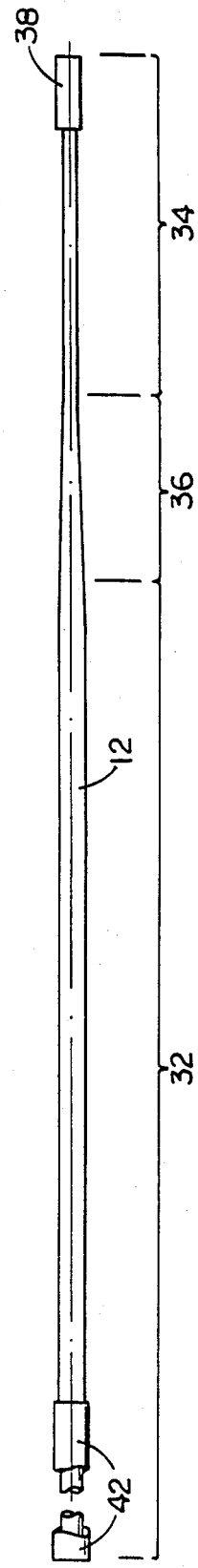
FIG. 2 is a top plan view of the core and sleeve of the guidewire of FIG. 1.

Referring to FIGS. 1 and 2, a guidewire 10 of the invention has an elongated core 12, a first coil 14 joined at its proximal end 16 to the core, and a second coil 18 joined to the distal end of the first coil at 20 and extending distally to a distal round end tip element 22, e.g., a weldment.

Figure 3:
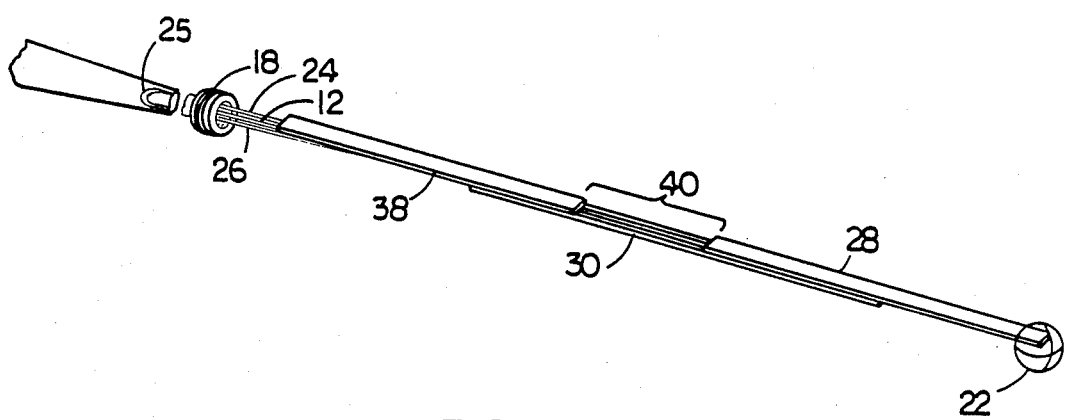
FIG. 3 is a perspective view partially in section of the distal tip region of the guidewire of FIG. 1.

Referring to FIG. 3, disposed within the distal portion of the first coil and extending along within the second coil, along the distal portion of the core, are safety wire 24 and transition wire 26, e.g., platinum wire, having a diameter of 0.003 inch., or a cross section of 0.002 inch by 0.005 inch. The safety and transition wires terminate distally in generally flat end portions 28, 30, respectively, e.g., about 10 mm long by 0.005 inch wide by 0.0012 inch thick, formed by flattening the ends of the wires. The distal end of the safety wire 24 extends and is joined, e.g., by soldering (or brazing, spot welding, bonding or T.I.G. (tungsten inert gas) welding), to the distal round end tip element 22. The transition wire 26 terminates distally within the second coil, spaced about 7 mm from tip element 22. In the preferred embodiment, the transition wire 26 and safety wire 24 are formed of a single wire, and may be joined proximally at loop 25 (FIG. 3). Both wires are attached to the core at the loop, about 6 inches from the distal tip, e.g., by soldering or the like.

The core 12, e.g., about 143 cms long, is formed, e.g., of stainless steel and has a body portion 32, e.g., 0.020 inch diameter, and a tip portion 34, e.g., 0.003 inch diameter and 8.0 cm long, with a smoothly tapering portion 36, e.g., about 5.5 cm long, therebetween. The body 32 of the core forms generally the body of the guidewire, while the tapering and tip portions 36, 34, in combination with the other components described define a distal tip region of relatively greater flexibility, the guidewire smoothly becoming more flexible in the direction of the tip. The tip portion 34 of the core terminates distally in a flat distal end 38, e.g. about 10 mm long by 0.005 inch wide by 0.0012 inch thick, formed by flattening the end of the core wire. The core extends distally within the second coil and terminates (FIG. 3) at a position spaced, e.g., about 10 mm from tip element 22.

As shown, the core wire is positioned to leave a gap 40 between the end portions 28, 38 of the safety wire 24 and the core 12, and the end portion 30 of the transition wire is disposed to bridge the gap. The result is a smooth transition of flexibility to the tip, as described more fully below with reference to FIG. 5.

Disposed about the proximal portion of the body of the core is a sleeve 42, e.g., polytetrafluoroethylene (PTFE) heat shrunk tightly about the core 12. Typically, prior to heat shrinking, the sleeve has a 0.060 inch outer diameter and 0.003 inch wall. The sleeve is diposed in position about the core and heated to 800° F., e.g., with a hot air blower or in an oven or by other suitable means, to shrink the sleeve to engage tightly about the core.

The first coil 14, e.g., made from stainless steel wire having a diameter of 0.007 inch formed into a pre-tension coil, has a proximal portion 44 with an outer diameter of about 0.035 inch and tapers in the region 46, corresponding generally to the tapering portion 36 of the core 12, to a distal portion 48 having an outer diameter of 0.025 inch. The coil 14 is joined to the core 12, e.g., by soldering or the like, at 16, adjacent the distal end of the sleeve 42. (The outer diameter of the sleeve is equal to or preferably less than the outer diameter of the coil, as shown.)

The second coil 18 is formed of a radioopaque material, e.g., platinum, for enhanced visibility within the body via radioscope. The coil 18 is a 0.003 inch diameter wire formed into a coil having an outer diameter at its proximal end (region 20) corresponding to the outer diameter of the adjacent end of first coil 14, e.g., 0.025 inch, and a consequent inner diameter of 0.019 inch. The second coil tapers (region 21) to a flexible proximal portion 19 about 30 mm long with an outer diameter of about 0.018 inch.

Figure 4:
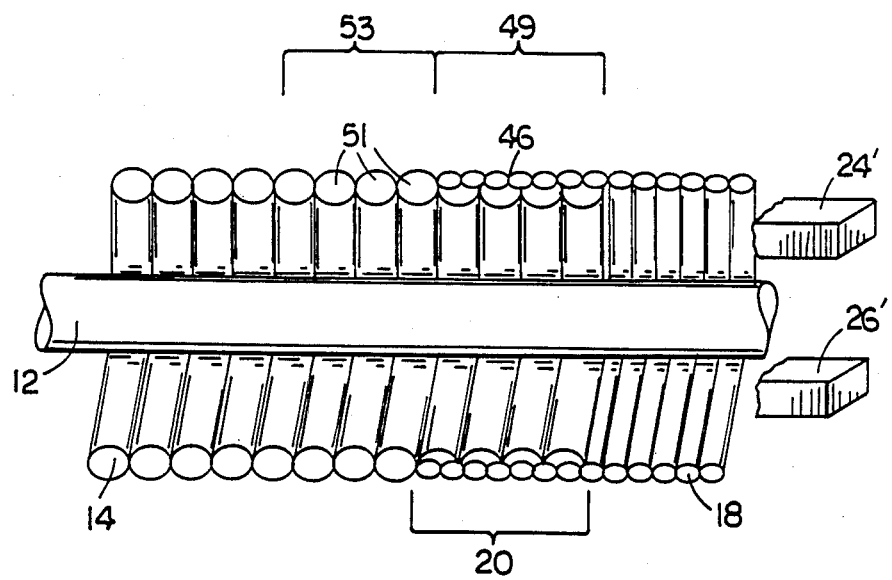
FIG. 4 is a side section view of the coil-to-coil joint.

Referring to FIG. 4, the first coil 14 and second coil 18 are joined by removing wire material from the outer diameter of the first coil, e.g., by grinding, to a depth substantially equal to the diameter or thickness of the wire forming the second coil. Preferably, the wires of the first and second coils are sized so no more than one half of the diameter of the first coil must be removed. As a result, removal of material from the exterior of the first coil provides a smooth flat surface for joining of the second coil and the windings of the first coil remain engaged under pretension. (Removal of more than one-half of the diameter will result in a soft, loose coil.) The proximal end of the second coil is disposed over the distal end 49 of the first coil in the region 20 and the two are joined, e.g., by solder 46 or the like. To further enhance the smoothness of the transition from the relatively stiff first coil 14 to the more flexible second coil 18, adjacent windings 51 of the first coil (region 53), proximal of the joint (region 20), are tweeked, i.e., spaced apart, to relieve the pretension set in forming and the windings are permanently deformed in the spaced condition, rendering the first coil relatively more flexible in the region approaching the joint and the considerably more flexible second coil.

Figure 5:
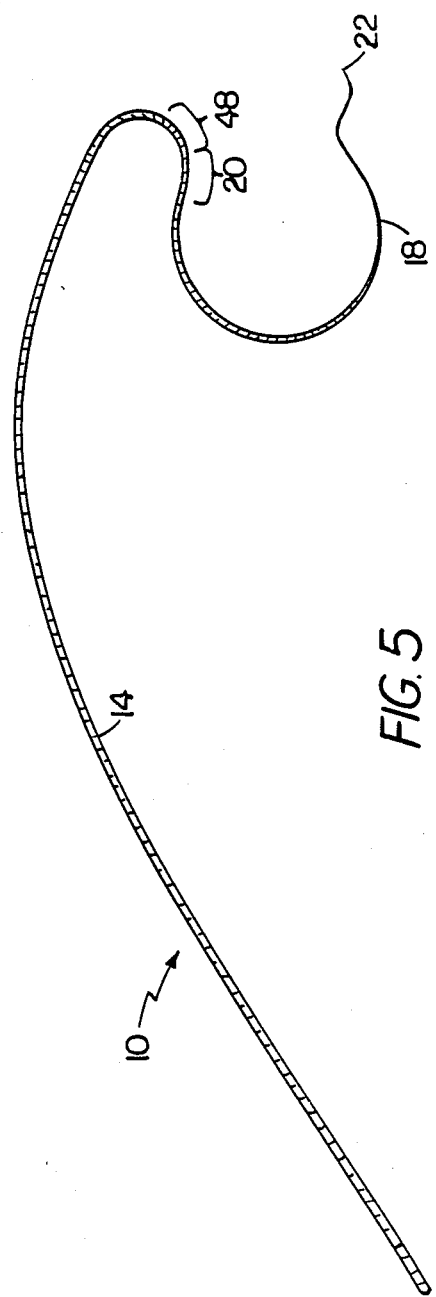
FIG. 5 is a somewhat diagrammatic representation of the guidewire flexed to show the smooth transition of flexibility.

The combination of structural features described above, including, without limitation, the materials and the relationships of dimension and construction, results in a guidewire that provides a high degree of torque i.e., approaching 1to1, between rotation of the proximal end and response of the distal tip, and further results in a guidewire having relatively smooth and gradual transition from the guidewire body to the relatively more flexible distal tip. Referring to FIG. 5, the guidewire 10 of the invention increases in flexibility in the distal tip region toward the tip.

Other embodiments are within the following claims. For example, referring to FIG. 4, the safety wire 24' and transition wire 26' may be one or a pair of flat ribbon wires. The safety and transition wires may be severed at 25 to lie side by side prior to being secured to the core.

What is claimed is:

1. A medical guidewire having an elongated body that has a degree of flexibility and a distal tip region of relatively greater flexibility, said guidewire comprising a core having a body portion of a first diameter, a distal portion of a relatively smaller diameter, and a generally flat distal end portion, said end portion disposed in said tip region and spaced proximally from a round tip element that defines a distal end of said guidewire, a first coil joined to the body portion of said core and extending along said core to a termination point in said distal tip region, proximal of the end portion of the core, a relatively more flexible second coil has a proximal end joined to said first coil and has a distal end joined to the round tip element, a safety wire secured to said core, said safety wire having a generally flat distal end portion within said second coil, joined to said round tip element, and a transition wire secured to said core, said transition wire having a generally flat distal end portion disposed to terminate within said second coil intermediate of the distal end portions of said core and of said safety wire.

2. The medical guidewire of claim 1 wherein the generally flat distal end portions of the core, safety wire and transition wire are of predetermined axial extent, and the generally flat distal end portion of said transition wire is disposed to span a gap between a proximal end of the safety wire generally flat distal end portion and a distal end of the core generally flat distal end portion.

3. The medical guidewire of claim 1 wherein at least one of said safety wire and said transition wire is a flat ribbon wire.

4. The medical guidewire of claim 1 wherein at least one of said safety wire, said transition wire, said second coil and said round tip element are of radioopaque material.

5. The medical guidewire of claim 1 wherein said radioopaque material comprises platinum.

6. The medical guidewire of claim 1 wherein said first coil in a first region preceding said second coil has a first outer diameter and in a second region distal said first region said first coil has a second, relatively smaller outer diameter, and said second coil, in a proximal region adjacent said first coil, has an outer diameter substantially equal to the first outer diameter of said first coil and an inner diameter substantially equal to the second outer diameter of said first coil, and the proximal region of said second coil is disposed about the second, smaller diameter region of said first coil.

7. The medical guidewire of claim 6 wherein the diameter of said first coil in said first region is substantially uniform, and the diameter of said first coil in said second region is substantially uniform, and said first region lies immediately adjacent said second region.

8. The medical guidewire of claim 6 wherein the relatively smaller second diameter of the second region of said first coil is formed by removal of coil wire material from the exterior of said coil.

9. The medical guidewire of claim 6 wherein said first coil and said second coil are joined in the proximal region of said second coil.

10. The medical guidewire of claim 1 or 6 wherein adjacent windings of said first coil in the region proximal of joining to said second coil are relatively more spaced than adjacent windings of other, more proximal regions of said first coil.

11. The medical guidewire of claim 1 wherein said first coil terminates distal of a proximal end of said core and said guidewire further comprises a sleeve of polymeric material disposed about said core.

12. The medical guidewire of claim 11 wherein the material of said sleeve is polytetrafluorethylene (PTFE).

13. The medical guidewire of claim 11 wherein the sleeve terminates distally adjacent a proximal end of said first coil and the outer diameter of said first coil adjacent said sleeve is equal to or greater than the outer diameter of the adjacent sleeve.

14. A medical guidewire comprising, in sequence, a first coil and a relatively more flexible second coil, said first coil in a first region preceding said second coil having a first outer diameter and in a second region distal said first region said first coil having a second, relatively smaller outer diameter, and said second coil, in a proximal region adjacent said first coil, having an outer diameter substantially equal to the first outer diameter of said first coil and an inner diameter substantially equal to the second outer diameter of said first coil, and the proximal region of said second coil is disposed about the second, smaller diameter region of said first coil.

15. The medical guidewire of claim 14 wherein the diameter of said first coil in said first region is substantially uniform, and the diameter of said first coil in said second region is substantially uniform, and said first region lies immediately adjacent said second region.

16. The medical guidewire of claim 14 wherein the relatively smaller second diameter of the second region of said first coil is formed by removal of coil wire material from the exterior of said coil.

17. A medical guidewire comprising, in sequence, a first coil and a relatively more flexible second coil, said first coil being formed of round wire, said first coil in a first region preceding said second coil having a substantially uniform first outer diameter and in a second region distal said first region said first coil having a second, relatively smaller, substantially uniform outer diameter formed by removal of coil wire material from the exterior of said coil, said first region lying immediately adjacent said second region, the difference between said first outer diameter and said second outer diameter being less than or equal to one-half the diameter of said round wire, and said second coil, in a proximal region adjacent said first coil, having an outer diameter substantially equal to the first outer diameter of said first coil and an inner diameter substantially equal to the second outer diameter of said first coil, and the proximal region of said second coil being disposed about the second, smaller diameter region of said first coil.

18. The medical guidewire of claim 17 wherein the wire of said second coil is round.

19. The medical guidewire of claim 14 or 17 wherein said first coil and said second coil are joined in the proximal region of said second coil.

20. The medical guidewire of claim 14 or 17 wherein adjacent windings of said first coil in the region proximal of joining to said second coil are relatively more spaced than adjacent windings of other, more proximal regions of said first coil.

21. The medical guidewire of claim 1, 6, 14 or 17 wherein said first coil has an outer portion of tapering diameter.

22. The medical guidewire of claim 1, 6, 14 or 17 wherein said second coil has an outer portion of tapering diameter.

* * * * *

UNITED STATES PATENT AND TRADEMARK OFFICE
CERTIFICATE OF CORRECTION

PATENT NO. : 4,830,023
DATED : May 16, 1989
INVENTOR(S) : de Toledo et al

It is certified that error appears in the above-identified patent and that said Letters Patent is hereby corrected as shown below:

Column 1, line 40, "add" should read --and--

Column 4, line 45, "1to1" should read --1-to-1--.

Column 4, line 56, "side by side" should read --side-by-side--.

Signed and Sealed this

Thirtieth Day of January, 1990

Attest:

JEFFREY M. SAMUELS

*Attesting Officer*    *Acting Commissioner of Patents and Trademarks*